United States Patent

Woelfle-Gupta et al.

(10) Patent No.: US 12,350,288 B2
(45) Date of Patent: Jul. 8, 2025

(54) INDUCING CASPASE ACTIVITY

(71) Applicant: Dow Global Technologies LLC, Midland, MI (US)

(72) Inventors: Caroline Woelfle-Gupta, Midland, MI (US); Andrew Scott, Midland, MI (US); Matthew LeBaron, Midland, MI (US); Daniel Wilson, Midland, MI (US); Susan L. Jordan, Doylestown, PA (US); Robert L. Schmitt, Harleysville, PA (US); Raja Settivari, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 817 days.

(21) Appl. No.: 17/435,545

(22) PCT Filed: Feb. 26, 2020

(86) PCT No.: PCT/US2020/019869
§ 371 (c)(1),
(2) Date: Sep. 1, 2021

(87) PCT Pub. No.: WO2020/180555
PCT Pub. Date: Sep. 10, 2020

(65) Prior Publication Data
US 2022/0054534 A1    Feb. 24, 2022

Related U.S. Application Data

(60) Provisional application No. 62/813,834, filed on Mar. 5, 2019.

(51) Int. Cl.
*A61K 31/765* (2006.01)
*A61K 31/795* (2006.01)
*A61P 35/00* (2006.01)

(52) U.S. Cl.
CPC .......... *A61K 31/765* (2013.01); *A61K 31/795* (2013.01); *A61P 35/00* (2018.01)

(58) Field of Classification Search
CPC ...... A61K 31/765; A61K 31/795; A61P 35/00
See application file for complete search history.

(56) References Cited

U.S. PATENT DOCUMENTS

| 10,533,046 | B2 * | 1/2020 | Albaret | .............. C07K 16/3061 |
| 2001/0051659 | A1 | 12/2001 | Corpet et al. | |
| 2014/0050724 | A1 | 2/2014 | Roy et al. | |
| 2016/0228467 | A1 | 8/2016 | Stein et al. | |

FOREIGN PATENT DOCUMENTS

| CN | 102961323 | * | 3/2013 | |
| FR | 2784896 | | 4/2000 | |
| WO | WO-2008064217 A2 | * | 5/2008 | ........... A61K 31/423 |

OTHER PUBLICATIONS

Bharadwai et al., "Higher Molecular Weight Polethykene Glycol Increase Cell Proliferation While improving Barrier Function in an In Vitro Colon Cancer model", Journal of Biomedicine and Biotechnology, vol. 2011, Article ID 587470, 7 pages. (Year: 2011).*
International Preliminary Report on Patentability for related PCT Application PCT/US2020/019869, mailed Sep. 16, 2021 (11 pgs).
International Search Report & Written Opinion for related PCT Application PCT/US2020/019869, mailed Jun. 16, 2020 (17 pgs).
Dorval, et al., "Polyethylene Glycol and Prevalence of Colorectal Adenomas"; Gastroenterol Clinical Biology, vol. 31, No. 10, Oct. 1, 2005 (4 pgs).
Galluzzi, et al., "Caspases Connect Cell-Death Signaling to Organismal Homeostasis"; Immunity Cell Press US, vol. 44, No. 2, Feb. 16, 2016 (12 pgs).
Dorval et al. "Polyethylene glycol and prevalence of colorectal adenomas." Gastroenterologie clinique et biologique vol. 30,10 (2006): 1196-9.
Galluzzi et al. "Caspases Connect Cell-Death Signaling to Organismal Homeostasis." Immunity vol. 44,2 (2016): 221-31.

* cited by examiner

*Primary Examiner* — Jianfeng Song
(74) *Attorney, Agent, or Firm* — Arthur R. Rogers

(57) ABSTRACT

Embodiments are directed towards methods of inducing caspase activity. The methods include contacting a cell with a treatment compound represented by the following Formula (I): where $R^1$ is selected from hydrogen or an alkyl group having from 1 to about 16 carbon atoms; $R^2$ is selected from a hydroxyl group, a tosylate group, an alkoxy group of the formula $OR^3$ where $R^3$ is selected from an alkyl group having from 1 to about 16 carbon atoms, or an ester group of the formula $OCOR^4$, where $R^4$ is an alkyl group having from 1 to about 16 carbon atoms, and n is from 4 to 46,000, with the proviso that when $R^1$ is hydrogen and $R^2$ is a hydroxy group the treatment compound has a number average molecular weight from 10,100 to 2,000,0000 g/mol.

9 Claims, No Drawings

INDUCING CASPASE ACTIVITY

This application is a National Stage Application under 35 U.S.C. § 371 of International Application Number PCT/US2020/019869, filed Feb. 26, 2020 and published as WO 2020/180555 on Sep. 10, 2020, which claims the benefit to U.S. Provisional Application 62/813,834, filed Mar. 5, 2019, the entire contents of which are incorporated herein by reference in its entirety

FIELD OF DISCLOSURE

Embodiments of the present disclosure are directed towards methods inducing caspase activity.

BACKGROUND

Cancer is a group of diseases involving abnormal cell growth. Colorectal cancer, which may be referred to as colon cancer or bowel cancer, is a cancer from uncontrolled cell growth in the colon or rectum.

Colorectal cancer is a commonly diagnosed malignancy. Treatments for colorectal cancer can include surgery, radiation therapy, and/or chemotherapy. However, there remains a need for new methods and/or new compositions that may be utilized for treatment.

SUMMARY

The present disclosure provides methods of inducing caspase activity, the method comprising contacting a cell with a treatment compound represented by the following Formula:

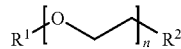

where $R^1$ is selected from hydrogen or an alkyl group having from 1 to about 16 carbon atoms; $R^2$ is selected from a hydroxyl group, a tosylate group, an alkoxy group of the formula $OR^3$ where $R^3$ is selected from an alkyl group having from 1 to about 16 carbon atoms, or an ester group of the formula $OCOR^4$, where $R^4$ is an alkyl group having from 1 to about 16 carbon atoms, and n is from 4 to 46,000, with the proviso that when $R^1$ is hydrogen and $R^2$ is a hydroxy group the treatment compound has a number average molecular weight from 10,100 to 2,000,0000 g/mol.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

While not intending to be bound to theory, one mechanism involved in the development of colorectal cancer is the mutation of the APC (Adenomatous Polyposis Coli) gene, which produces the APC protein. The APC protein is part of a protein-based destruction complex that helps to prevent the accumulation of the β-catenin protein in a cell. The APC protein and the β-catenin protein are part of one of the WNT (Wingless/Integrated) signaling transduction pathways that pass signals into a cell through cell surface receptors. In general, when cells are stimulated by WNT, the destruction complex is deactivated, and β-catenin protein will enter the nucleus and bind to the transcription factor (TCF) which controls the transcription of genetic information. The genes involved in regular cell progression will be activated and it is a regulated process. Without the APC protein, β-catenin protein will continuously accumulate to high levels and translocate into the nucleus, bind to the TCF, which can then bind to DNA, and activate the transcription of proto-oncogenes. When proto-oncogenes are inappropriately expressed at high levels, they can become oncogenes. Activated oncogenes can cause cells designated for apoptosis to survive and proliferate instead, which can lead to the development of colorectal cancer in an individual.

Methods of inducing caspase activity are disclosed herein. Advantageously, inducing caspase activity can incite apoptosis, i.e. induce cell death. For a number of applications, apoptosis is desirable, as compared to necrosis. Inducing caspase activity can provide for degradation of a number of intracellular proteins to result in cell death. Cell death by apoptosis can be a desirable effect on colorectal cancer cells, for instance.

As used herein, "a", "an", "the", "at least one", "a number of", and "one or more" may be used interchangeably unless indicated otherwise. The term "and/or" means one, one or more, or all of the listed items. The recitations of numerical ranges by endpoints include all numbers subsumed within that range, e.g., 1 to 5 includes 1, 1.5, 2, 2.75, 3, 3.80, 4, 5, etc.

The methods of inducing caspase activity, as disclosed herein, include contacting a cell, e.g., a plurality of cells, with a treatment compound. As used herein, "treatment compound" refers to compounds that may be represented by the following Formula I:

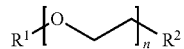

Formula I where $R^1$ is selected from hydrogen or an alkyl group having from 1 to about 16 carbon atoms; $R^2$ is selected from a hydroxyl group, a tosylate group, an alkoxy group of the formula $OR^3$ where $R^3$ is selected from an alkyl group having from 1 to about 16 carbon atoms, or an ester group of the formula $OCOR^4$, where $R^4$ is an alkyl group having from 1 to about 16 carbon atoms, and n is from 4 to 46,000, with the proviso that when $R^1$ is hydrogen and $R^2$ is a hydroxy group the treatment compound has a number average molecular weight from 10,100 to 2,000,0000 g/mol.

As mentioned, each of $R^1$, $R^3$, and $R^4$ may be an alkyl group having from 1 to about 16 carbon atoms. For instance, the alkyl groups of $R^1$, $R^3$, and $R^4$ may each independently include 1, 2, 3, 4, 5, 6, 7, 8, 9, 10, 11, 12, 13, 14, 15, or 16 carbon atoms. The alkyl groups of $R^1$, $R^3$, and $R^4$ may each independently be saturated or unsaturated alkyl groups. The alkyl groups of $R^1$, $R^3$, and $R^4$ may each independently be linear or branched alkyl groups.

One or more embodiments of the present disclosure provide that the treatment compound may be represented by the following Formula II:

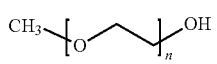

Formula II where n is from 4 to 46,000. Treatment compounds represented by Formula II may be referred to as poly(ethylene glycol) methyl ethers.

One or more embodiments of the present disclosure provide that the treatment compound may be represented by the following Formula III:

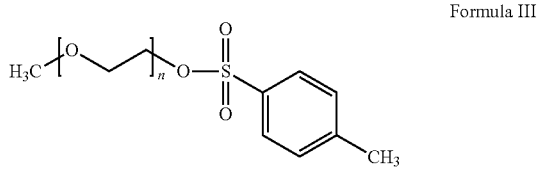

Formula III where n is from 4 to 46,000. Treatment compounds represented by Formula III may be referred to as poly(ethylene glycol) methyl ether tosylates.

Embodiments of the present disclosure provide that the treatment compound has a number average molecular weight (Mn) from 200 to 2,000,000 g/mol. All individual values and subranges from 200 to 2,000,0000 g/mol are included; for example, the treatment compound can have Mn from a lower limit of 200, 300, 400, or 500 g/mol to an upper limit of 2,000,0000; 1,750,0000; 1,500,0000; 1,250,0000; or 1,000,0000 g/mol.

Embodiments of the present disclosure provide that when $R^1$ is hydrogen and $R^2$ is a hydroxy group of the treatment compound represented by Formula I, the treatment compound has a number average molecular weight from 10,100 to 2,000,0000 g/mol. All individual values and subranges from 10,100 to 2,000,0000 g/mol are included; for example, when $R^1$ is hydrogen and $R^2$ is a hydroxy group of the treatment compound represented by Formula I, the treatment compound can have Mn from a lower limit of 10,100; 10,500; 11,000; 15,000; 20,000; 35,000; 50,000; 75,000; or 100,000 g/mol to an upper limit of 2,000,0000; 1,750,0000; 1,500,0000; 1,250,0000; or 1,000,0000 g/mol.

The treatment compound may be prepared using known methods, equipment, and/or conditions, which may vary for different applications. The treatment compound may be obtained commercially.

As mentioned, methods of inducing caspase activity, as disclosed herein, include contacting a cell with the treatment compound. One or more embodiments of the present disclosure provide that contacting the cell with the treatment compound occurs in vivo. One or more embodiments of the present disclosure provide that contacting the cell with the treatment compound occurs in vitro. The cell may be contacted with the treatment compound by utilizing a number of different known methods, equipment, and/or conditions. Various methods, equipment, and/or conditions may be utilized for different applications The treatment compound may be utilized with a known treatment medium. For instance, the treatment compound may be dissolved, to provide an effective amount, in a known treatment medium prior to contacting the cell. One or more embodiments provide that the treatment compound and the treatment medium may be combined to form a solution. The solution may be a homogeneous solution. Examples of treatment mediums include, but are not limited to, DMEM (Dulbecco's Modified Eagle Medium), RPMI 1640, and McCoy's 5A, and combinations thereof, among others. A number of treatment mediums are commercially available.

The treatment compound can have a 0.001 millimolar (mM) to 75 mM concentration in the treatment medium. All individual values and subranges from 0.001 to 75 mM are included; for example, the effective concentration can be from a lower limit of 0.001, 0.005, 0.01, 0.1 or 1.0 mM to an upper limit of 75, 72, 70, 68, or 65 mM of the treatment compound in the treatment medium.

The cell may be contacted with an effective amount of the treatment compound. As used herein, the term "effective amount", which may be used interchangeably with "therapeutic effective amount" and/or "therapeutic amount", refers to an amount of the treatment compound that is sufficient to provide the intended application, e.g., induce caspase activity. Contacting the cell with an effective amount of the treatment compound may desirably provide a disease treatment, e.g., a colorectal cancer treatment, where undesirable cells are subject to cell death by apoptosis that results from inducing caspase activity. The effective amount may vary depending upon the particular application, e.g., in vitro or in vivo, the subject being treated, e.g., the weight and age of the subject, the severity of the disease condition, and/or the manner of administration, among other considerations, which can readily be determined by one of ordinary skill in the art. As used herein, a "subject" that is treated refers to any member of the animal kingdom, e.g., mammals, including humans.

Embodiments of the present disclosure provide that specific doses may vary depending on the particular treatment compound utilized, the dosing regimen to be followed, timing of administration, and/or the physical delivery system in which the treatment compound is carried. For instance, the effective amount of the treatment compound may be contacted with the cell by a single dosing or by multiple dosings.

Embodiments of the present disclosure provide that the cell that is contacted with the treatment compound is a cancerous cell. For instance, the cell may be a colorectal cancer cell. Colorectal cancer cells may also be referred to as colon cancer cells, bowel cancer cells, and/or colorectal adenocarcinoma cells. One or more embodiments of the present disclosure provide that additional cells, i.e. non-cancerous cells, may be contacted with the treatment compound.

While not intending to be bound by theory, caspases, which may be referred to as cysteine-aspartic acid proteases, are a family of cysteine proteases involved in apoptosis. There are two types of caspases: initiator caspases, which include caspase 2,8,9,10,11,12, and effector caspases, which include caspase 3,6,7. One or more embodiments of the present disclosure provide that contacting a cell with a treatment compound induces an effector caspase activity. One or more embodiments of the present disclosure provide that the caspase is selected from caspase 3, caspase 6, caspase 7, or combinations thereof.

As mentioned, inducing caspase activity can advantageously incite apoptosis. Induced caspase activity may be determined by a number of different known methods, equipment, and/or conditions. For instance, induced caspase activity may be evidenced by an average relative caspase activity greater than one (>1), e.g., for a number of experimental runs, as determined by Caspase-Glo 3/7 Assay 4.B. Standard Protocol for Cells in a 96-Well Plate, available from Promega. As used herein, "relative caspase activity" can be utilized interchangeably with relative apoptosis.

Utilizing the treatment compound, as discussed herein, may advantageously provide an improved, i.e. reduced, laxative effect, as compared to some other polymeric compounds utilized for cancer treatment. This reduced laxative effect may help to provide a desirable increase with patient compliance, as compared to some other polymeric compounds associated with a relatively greater laxative effect.

One or more embodiments of the present disclosure provide a method of treating colorectal cancer. The method can include contacting a colorectal cancer cell with the treatment compound.

One or more embodiments of the present disclosure provide a method of treating cancer. The method can include administering the treatment compound to a mammal.

EXAMPLES

In the Examples, various terms and designations for materials are used including, for instance, the following:

Poly(ethylene glycol) methyl ether (Mn 2000 g/mol; obtained from Sigma-Aldrich);

Poly(ethylene glycol) methyl ether (Mn 5000 g/mol; obtained from Sigma-Aldrich);

Poly(ethylene glycol) methyl ether tosylate (Mn 2000 g/mol; obtained from Sigma-Aldrich);

Poly(ethylene glycol) methyl ether tosylate (Mn 5000 g/mol; obtained from Sigma-Aldrich);

POLYOX N12K (polyethylene glycol, Mn 1,000,000 g/mol; obtained from Dupont);

POLYOX VSR N750 (polyethylene glycol, Mn 300,000 g/mol; obtained from Dupont);

POLYOX VSR N3000 (polyethylene glycol, Mn 400,000 g/mol; obtained from Dupont);

Cells (human colon; colorectal adenocarcinoma; HT-29 (ATCC® HTB-3); obtained from ATCC);

McCoy's 5A (growth medium; obtained from ThermoFisher Scientific);

Fetal bovine serum (obtained from ATCC);

Dulbecco's Phosphate-Buffered Saline (GIBCO 14190-144; obtained from ThermoFisher Scientific);

Complete Growth Medium (ATCC® 30-2007; obtained from ATCC);

Trypsin-EDTA (GIBCO Trypsin-EDTA (0.25%); Catalog number 25200056; obtained from ThermoFisher Scientific);

Thiazolyl Blue Tetrazolium Bromide (obtained from ThermoFisher Scientific);

Dulbecco's Phosphate-Buffered Saline with calcium and magnesium (GIBCO 14040-133; obtained from ThermoFisher Scientific);

Caspase-Glo 3/7 Assay (luminescent assay; Catalog number G8093; obtained from Promega);

Dimethyl sulfoxide (Catalog number 276855; obtained from Sigma-Aldrich).

Culture Initiation and Maintenance

Culture initiation and maintenance was performed as follows. Culture initiation and maintenance was performed in accordance with "Thawing, Propagating, and Cryopreserving Protocol" NCI-PBCF-HTB38 (HT-29) Colon Adenocarcinoma (ATCC® HTB-38™); Feb. 27, 2012; Version 1.6.

HT-29 (ATCC® HTB-38™) cells (which contained approximately 1×10$^6$ cells per mL) were initiated and seeded into a T-25 flask containing McCoy's 5A and fetal bovine serum (10% (v/v)). Then, ATCC® 30-2007 (warmed in 37° C. water bath for at least 15 minutes) was used to expand the HT-29 cells. The cells were grown in a humidified incubator (SANYO INCT-16-CMT; MCO-19AIC (UV)) maintained at 37° C. and 5% $CO_2$. Then, the cells were rinsed with 1× Dulbecco's Phosphate-Buffered Saline and sub-cultured in T-75 flasks 1 to 3 times per week using 1× Trypsin-EDTA, applied for ≤5 minutes; enzymatic action of the trypsin-EDTA was stopped by adding complete growth medium to the detached cells. Then, upon reaching 80 to 90% confluency the cells were split into the following split ratio ranges: 1:5 to 1:16. Subculture and growth expansion activities were recorded, such as passage number, % confluency, % viability (only on experimental set-up day), and cell morphology throughout all phases. The cells were maintained in log-phase growth.

Cell Culture Plating (Day 0)

Cell culture plating was performed as follows. A cell suspension from a single 80 to 90% confluent T-75 flask was harvested with trypsin-EDTA and complete growth medium. To obtain cell concentration and viability, cell counts were obtained using a COUNTESS automated cell counter (INVITROGEN C10227; CNTR-7-CMT) in which 2 chambers of each slide were provided with 10 µL each of 1:1, 0.4% trypan-blue dye (INVITROGEN T10282) and cell suspension. Cell counts and percent viability were averaged from both chambers of a single slide. Then, viable cells (defined as viability≥90%) containing complete growth medium were plated onto sterile 96-well plates using a multi-channel pipette. Per cell density, between 5000 and 6000 cells per well (40,000 to 48,000 cells per mL) were added to each well, except for wells that were utilized as 'saline only' no cell control wells; equal volumes each of 125 µL of cell suspension were added per well beginning with row A to H on the plate. The plates used for each of 2 endpoints, apoptosis and cytotoxicity, were solid white plates and clear plates, respectively. The cells were incubated for 24±2 hours to allow attachment.

Poly(Ethylene Glycol) Methyl Ether/Poly(Ethylene Glycol) Methyl Ether Tosylate/Polyethylene Glycol Stock Preparations Stock solutions were prepared at target concentrations of poly(ethylene glycol) methyl ether, poly(ethylene glycol) methyl ether tosylate, and polyethylene glycol in sterile saline. For the assays, based on the solubility limits due to high molecular weight, adjustments to lower stock concentration preparations (w/v) to generate either a solution or a pipettable suspension were made if necessary, or solubilization was achieved by adding small increments of saline, continuous mixing, vortexing, sonicating, or stirring prior to use in assay. If necessary for solubilization, the saline was pre-heated to 37° C. prior to mixing with the poly(ethylene glycol) methyl ether, poly(ethylene glycol) methyl ether tosylate, and/or polyethylene glycol. Total volumes of 10 mL were prepared per tested substance on the day of cell suspension plating (Day 0).

Cytotoxicity Reagent Preparation

Thiazolyl blue tetrazolium bromide was prepared at 5 mg/mL in Dulbecco's Phosphate-Buffered Saline with calcium and magnesium. Total volumes of 30 mL were prepared (w/v) per set-up day (Day 0) and stored at 4° C. until use.

Dosing Solution Preparation (Day 0)

Dosing solutions/suspensions of each test substance stock were prepared in a total of 15 mL each of McCoy's 5A and 1% fetal bovine serum. Various amounts of dosing stock were utilized to achieve dosing solutions/suspensions from 0.0015 to 60 mM. The dosing solutions/suspensions were prepared in sterile reservoirs and repeatedly mixed with a pipette until visible uniformity was achieved. Using a 2 mL capacity sterile 96-deep well block, 2 mL of the dosing solution/suspension was added to each of 6 replicate wells for the treatment groups and each of 12 wells for the saline only cell controls and saline only 'no cell' background correction controls. The plates were established following a semi-randomized statistical design. Each test substance was identified numerically and via a color code used for identifying wells to be treated. The blocks were covered with sealing tape, plate lid and placed into a 4° C. lab refrigerator (Fischer Scientific, 135B1; RFR-22-CMT) overnight.

Treatment (Day 1)

All 96-deep well blocks containing dosing solutions/suspensions were removed from the refrigerator and placed in a 37° C. bead bath for a minimum of 30 minutes. Approximately 24 hours after plating, well plates were removed from the incubator and treated one at a time. All wells from a cell plate were aspirated using a 6-well aspirating device starting with row A to H. Using a multi-channel pipette, 100 each of dosing solution/suspension (from the blocks) was added to each well of the 96-well cell treatment plate; starting from row A to row H (same order). All wells were aspirated and treated 2 rows at a time to prevent well drying and maintain cell attachment and viability; pipette tips were changed per row. All plates were placed into the incubator and allowed to treat for 24±2 or 48±2 hours prior to harvest.

Harvest (Day 2 and Day 3)

Apoptosis

Assessment of apoptosis was performed as follows. Apoptosis was performed in accordance with "Caspase-Glo 3/7 Assay" 4.B. Standard Protocol for Cells in a 96-Well Plate (Promega). The Caspase-Glo 3/7 Assay components were pre-warmed to room temperature for approximately 60 minutes. White plates were removed (one at a time) from the incubator and the treatment medium was aspirated. Using a multi-channel pipette, 100 μL of 1× Dulbecco's Phosphate-Buffered Saline was added to each well of the 96-well plate. The Assay reagents (buffer and substrate) were manually mixed and added to a reagent reservoir; using a multi-channel pipette, 100 μL of the Assay reagent mixture was added to each well of the 96-well plate. The plate(s) (protected with foil from light) were placed on a plate shaker and allowed to rotate for 5 minutes at approximately 800 rpm at room temperature. The plates were then incubated at room temperature for an additional 25 minutes prior to analysis. Luminescence was recorded in terms of Relative Light Units (RLU) for each plate on a FLUOstar Omega Plate Reader.

Cytotoxicity

Assessment of cytotoxicity was performed as follows. Cytotoxicity reagent (5 mg/mL), as previously described, was pre-warmed to room temperature for approximately 30 minutes and then diluted into 1× Dulbecco's Phosphate-Buffered Saline with calcium and magnesium to provide a concentration of 0.675 mg/mL (final). Clear plates were removed from the incubator (one at a time) and the treatment medium was aspirated. Using a multi-channel pipette, 200 μL of the cytotoxicity reagent (final) was added to each well of the 96-well plate; then the plates were covered with sealing tape and incubated in a humidified 37° C. incubator for 4 hours. Following incubation, the supernatant was aspirated and dimethyl sulfoxide (200 μL) was added to each well. Following thorough mixing by repeat pipetting, the cell lysate was transferred to a new clear 96-well plate and absorbance was quantified at 600 and 630 nm on a FLUOstar Omega Plate Reader.

Analysis

Relative Caspase Activity (Please Provide a Definition for this)

Relative caspase activity was calculated as follows: $(RLU_{Foreground}) - (RLU_{Saline\ Only\ 'no\ cell'\ control}) = (RLU_{Background\ corrected})$;

$((RLU_{Background\ corrected})$ of each test substance containing well)/(Average $(RLU_{Foreground})$ of 12 saline only control wells)=relative caspase activity; where RLU=relative light unit.

Relative caspase activity of each test substance containing well/6 replicates=Average relative caspase activity. The results are reported in Tables 1, 3, 5, 7, 9, 11, and 13 for the various utilized concentrations.

Cell viability was calculated as follows:

$$(Abs_{600\ Foreground}) - (Abs_{600\ Saline\ Only\ 'no\ cell'\ control}) = (Abs_{600\ Background\ corrected})$$

$$(Abs_{630\ Foreground}) - (Abs_{630\ Saline\ Only\ 'no\ cell'\ control}) = (Abs_{630\ Background\ corrected})$$

$$(Abs_{600\ Background\ corrected}) - (Abs_{630\ Background\ corrected}) = (Abs_{600\text{-}630})$$

$((Abs_{600\text{-}630})$ of each test substance containing well)/(Average $(Abs_{600\text{-}630})$ of 12 saline only control wells)=% Cell Viability % Cell Viability of each test substance containing well/6 replicates=Average % Cell Viability. The results are reported in Tables 2, 4, 6, 8, 10, 12, and 14 for the various utilized concentrations.

TABLE 1

|  | Poly(ethylene glycol) methyl ether Mn 2000 g/mol [15 mM] | Poly(ethylene glycol) methyl ether Mn 2000 [30 mM] | Poly(ethylene glycol) methyl ether g/mol Mn 2000 g/mol [60 mM] |
|---|---|---|---|
| Average relative caspase activity (Run 1) | 1.36 | 1.19 | 0.91 |
| Standard deviation relative caspase activity (Run 1) | 0.14 | 0.12 | 0.07 |
| Average relative caspase activity (Run 2) | 1.24 | 1.24 | 1.07 |
| Standard deviation relative caspase activity (Run 2) | 0.11 | 0.07 | 0.06 |

TABLE 1-continued

|  | Poly(ethylene glycol) methyl ether Mn 2000 g/mol [15 mM] | Poly(ethylene glycol) methyl ether Mn 2000 [30 mM] | Poly(ethylene glycol) methyl ether g/mol Mn 2000 g/mol [60 mM] |
| --- | --- | --- | --- |
| Average relative caspase activity (Run 3) | 1.31 | 1.29 | 1.23 |
| Standard deviation relative caspase activity (Run 3) | 0.14 | 0.12 | 0.20 |
| Average relative caspase activity (Runs 1, 2, 3) | 1.30 | 1.24 | 1.07 |
| Standard deviation relative caspase activity (Runs 1, 2, 3) | 0.06 | 0.05 | 0.16 |

The data of Table 1 illustrate that advantageous relative caspase activities, i.e. average relative caspase activity >1, were provided when cells were exposed to 15, 30, and 60 mM concentrations of poly(ethylene glycol) methyl ether having a Mn of 2000 g/mol, as indicted by the respective average relative caspase activity (Runs 1, 2, 3) values.

TABLE 2

|  | Poly(ethylene glycol) methyl ether Mn 2000 g/mol [15 mM] | Poly(ethylene glycol) methyl ether Mn 2000 g/mol [30 mM] | Poly(ethylene glycol) methyl ether Mn 2000 g/mol [60 mM] |
| --- | --- | --- | --- |
| Average viability % (Run 1) | 112 | 93 | 68 |
| Standard deviation viability % (Run 1) | 12 | 14 | 22 |
| Average viability % (Run 2) | 168 | 128 | 117 |
| Standard deviation viability % (Run 2) | 59 | 27 | 23 |
| Average viability % (Run 3) | 86 | 174 | 47 |
| Standard deviation viability % (Run 3) | 24 | 29 | 10 |
| Average viability % (Runs 1, 2, 3) | 122 | 132 | 77 |
| Standard deviation viability % (Runs 1, 2, 3) | 42 | 41 | 36 |

The data of Table 2 illustrate that adequate viability, i.e. average viability % of 70% or greater, for average viability % (Runs 1, 2, 3) were provided after 24 hours when cells were exposed to 15, 30, and 60 mM concentrations of poly(ethylene glycol) methyl ether having a Mn of 2000 g/mol.

TABLE 3

|  | Poly(ethylene glycol) methyl ether Mn 5000 g/mol [1.5 mM] | Poly(ethylene glycol) methyl ether Mn 5000 g/mol [3 mM] | Poly(ethylene glycol) methyl ether Mn 5000 g/mol [6 mM] |
| --- | --- | --- | --- |
| Average relative caspase activity (Run 1) | 1.20 | 1.29 | 1.32 |

TABLE 3-continued

|  | Poly(ethylene glycol) methyl ether Mn 5000 g/mol [1.5 mM] | Poly(ethylene glycol) methyl ether Mn 5000 g/mol [3 mM] | Poly(ethylene glycol) methyl ether Mn 5000 g/mol [6 mM] |
| --- | --- | --- | --- |
| Standard deviation relative caspase activity (Run 1) | 0.08 | 0.06 | 0.09 |
| Average relative caspase activity (Run 2) | 1.05 | 0.96 | 0.85 |
| Standard deviation relative caspase activity (Run 2) | 0.07 | 0.50 | 0.23 |
| Average relative caspase activity (Runs 1, 2) | 1.13 | 1.13 | 1.09 |
| Standard deviation relative caspase activity (Runs 1, 2) | 0.11 | 0.23 | 0.33 |

The data of Table 3 illustrate that advantageous relative caspase activities, i.e. average relative caspase activity >1, were provided when cells were exposed to 1.5, 3, and 6 mM concentrations of poly(ethylene glycol) methyl ether having a Mn of 5000 g/mol, as indicted by the respective average relative caspase activity (Runs 1, 2) values.

TABLE 4

|  | Poly(ethylene glycol) methyl ether Mn 5000 g/mol [1.5 mM] | Poly(ethylene glycol) methyl ether Mnb5000 g/mol [3 mM] | Poly(ethylene glycol) methyl ether Mn 5000 g/mol [6 mM] |
| --- | --- | --- | --- |
| Average viability % (Run 1) | 158 | 163 | 136 |
| Standard deviation viability % (Run 1) | 27 | 15 | 27 |
| Average viability % (Run 2) | 143 | 118 | 93 |
| Standard deviation viability % (Run 2) | 20 | 24 | 14 |
| Average viability % (Runs 1, 2) | 151 | 141 | 115 |
| Standard deviation viability % (Runs 1, 2) | 11 | 32 | 30 |

The data of Table 4 illustrate that that adequate viability, i.e. average viability % of 70% or greater, for average viability % (Runs 1, 2) were provided after 24 hours when cells were exposed to 1.5, 3, and 6 mM concentrations of poly(ethylene glycol) methyl ether having a Mn of 5000 g/mol.

TABLE 5

|  | Poly(ethylene glycol) methyl ether tosylate Mn 2000 g/mol [15 mM] | Poly(ethylene glycol) methyl ether tosylate Mn 2000 g/mol [30 mM] |
| --- | --- | --- |
| Average relative caspase activity (Run 1) | 1.30 | 1.76 |
| Standard deviation relative caspase activity (Run 1) | 0.06 | 0.42 |
| Average relative caspase activity (Run 2) | 1.25 | 1.39 |
| Standard deviation relative caspase activity (Run 2) | 0.34 | 0.09 |
| Average relative caspase activity (Run 3) | 1.21 | 1.87 |
| Standard deviation relative caspase activity (Run 3) | 0.11 | 0.22 |
| Average relative caspase activity (Run 4) | 1.14 | 1.50 |
| Standard deviation relative caspase activity (Run 4) | 0.09 | 0.08 |
| Average relative caspase activity (Runs 1, 2, 3, 4) | 1.23 | 1.63 |
| Standard deviation relative caspase activity (Runs 1, 2, 3, 4) | 0.07 | 0.55 |

The data of Table 5 illustrate that advantageous relative caspase activities, i.e. average relative caspase activity >1, were provided when cells were exposed to 15, and 30 mM concentrations of poly(ethylene glycol) methyl ether tosylate having a Mn of 2000 g/mol, as indicted by the respective average relative caspase activity (Runs 1, 2, 3, 4) values.

TABLE 6

|  | Poly(ethylene glycol) methyl ether tosylate Mn 2000 g/mol [15 mM] | Poly(ethylene glycol) methyl ether tosylate Mn 2000 g/mol [30 mM] |
| --- | --- | --- |
| Average viability % (Run 1) | 86 | 72 |
| Standard deviation viability % (Run 1) | 21 | 23 |
| Average viability % (Run 2) | 82 | 54 |
| Standard deviation viability % (Run 2) | 51 | 8 |
| Average viability % (Run 3) | 99 | 58 |
| Standard deviation viability % (Run 3) | 22 | 16 |
| Average viability % (Run 4) | 38 | 43 |
| Standard deviation viability % (Run 4) | 15 | 24 |
| Average viability % (Runs 1, 2, 3, 4) | 76 | 57 |
| Standard deviation viability % (Runs 1, 2, 3, 4) | 27 | 12 |

The data of Table 6 illustrate that adequate viability, i.e. average viability % of 70% or greater, for average viability % (Runs 1, 2, 3, 4) were provided after 24 hours when cells were exposed to 15 and 30 mM concentrations of poly(ethylene glycol) methyl ether tosylate having a Mn of 2000 g/mol.

TABLE 7

|  | Poly(ethylene glycol) methyl ether tosylate Mn 5000 g/mol [1.5 mM] | Poly(ethylene glycol) methyl ether tosylate Mn 5000 g/mol [3 mM] | Poly(ethylene glycol) methyl ether tosylate Mn 5000 g/mol [6 mM] |
| --- | --- | --- | --- |
| Average relative caspase activity (Run 1) | 1.36 | 1.32 | 1.58 |
| Standard deviation relative caspase activity (Run 1) | 0.10 | 0.16 | 0.24 |
| Average relative caspase activity (Run 2) | 1.28 | 1.15 | 1.35 |
| Standard deviation relative caspase activity (Run 2) | 0.31 | 0.12 | 0.49 |

TABLE 7-continued

|  | Poly(ethylene glycol) methyl ether tosylate Mn 5000 g/mol [1.5 mM] | Poly(ethylene glycol) methyl ether tosylate Mn 5000 g/mol [3 mM] | Poly(ethylene glycol) methyl ether tosylate Mn 5000 g/mol [6 mM] |
|---|---|---|---|
| Average relative caspase activity (Runs 1, 2) | 1.32 | 1.24 | 1.47 |
| Standard deviation relative caspase activity (Runs 1, 2) | 0.06 | 0.12 | 0.16 |

The data of Table 7 illustrate that advantageous relative caspase activities, i.e. average relative caspase activity>1, were provided when cells were exposed to 1.5, 3, and 6 mM concentrations of poly(ethylene glycol) methyl ether tosylate having a Mn of 5000 g/mol, as indicted by the respective average relative caspase activity (Runs 1, 2) values.

TABLE 8

|  | Poly(ethylene glycol) methyl ether tosylate Mn 5000 g/mol [1.5 mM] | Poly(ethylene glycol) methyl ether tosylate Mn 5000 g/mol [3 mM] | Poly(ethylene glycol) methyl ether tosylate Mn 5000 g/mol [6 mM] |
|---|---|---|---|
| Average viability % (Run 1) | 140 | 118 | 65 |
| Standard deviation viability % (Run 1) | 17 | 14 | 8 |
| Average viability % (Run 2) | 109 | 128 | 57 |
| Standard deviation viability % (Run 2) | 36 | 14 | 4 |
| Average viability % (Runs 1, 2) | 125 | 123 | 61 |
| Standard deviation viability % (Runs 1, 2) | 22 | 7 | 6 |

The data of Table 8 illustrate that adequate viability, i.e. average viability % of 70% or greater for average viability % (Runs 1, 2) were provided after 24 hours when cells were exposed to 1.5, 3, and 6 mM concentrations of poly(ethylene glycol) methyl ether tosylate having a Mn of 5000 g/mol.

TABLE 9

|  | POLYOX N12K [0.0015 mM] | POLYOX N12K [0.003 mM] | POLYOX N12K [0.006 mM] |
|---|---|---|---|
| Average relative caspase activity (Run 1) | 1.23 | 1.25 | 1.72 |
| Standard deviation relative caspase activity (Run 1) | 0.25 | 0.08 | 0.17 |

The data of Table 9 illustrate that advantageous relative caspase activities, i.e. average relative caspase activity>1, were provided when cells were exposed to 0.0015, 0.003, and 0.006 mM concentrations of polyethylene glycol having a Mn of 1,000,000 g/mol, as indicted by the average relative caspase activity (Run 1) values.

TABLE 10

|  | POLYOX ® N12K [0.0015 mM] | POLYOX ® N12K [0.003 mM] | POLYOX ® N12K [0.006 mM] |
|---|---|---|---|
| Average viability % (Run 1) | 76 | 76 | 113 |
| Standard deviation viability % (Run 1) | 29 | 20 | 8 |

The data of Table 10 illustrate that adequate viability, i.e. average viability % of 70% or greater for average viability % (Run 1) were provided after 24 hours when cells were exposed to 0.0015, 0.003, and 0.006 mM concentrations of polyethylene glycol having a Mn of 1,000,000 g/mol.

TABLE 11

|  | POLYOX VSR N750 [0.003 mM] | POLYOX VSR N750 [0.006 mM] |
|---|---|---|
| Average relative caspase activity (Run 1) | 1.19 | 1.88 |
| Standard deviation relative caspase activity (Run 1) | 0.09 | 0.2 |

The data of Table 11 illustrate that advantageous relative caspase activities, i.e. average relative caspase activity>1, were provided when cells were exposed to 0.003 and 0.006 mM concentrations of polyethylene glycol having a Mn of 300,000 g/mol, as indicted by the average relative caspase activity (Run 1) values.

TABLE 12

|  | POLYOX VSR N750 [0.003 mM] | POLYOX VSR N750 [0.006 mM] |
|---|---|---|
| Average viability % (Run 1) | 98 | 89 |
| Standard deviation viability % (Run 1) | 49 | 7 |

The data of Table 12 illustrate that adequate viability, i.e. average viability % of 70% or greater for average viability % (Run 1) were provided after 24 hours when cells were exposed to 0.003 and 0.006 mM concentrations of polyethylene glycol having a Mn of 300,000 g/mol.

TABLE 13

|  | POLYOX VSR N3000 [0.0015 mM] | POLYOX VSR N3000 [0.006 mM] |
|---|---|---|
| Average relative caspase activity (Run 1) | 1.21 | 1.51 |
| Standard deviation relative caspase activity (Run 1) | 0.07 | 0.52 |

The data of Table 13 illustrate that advantageous relative caspase activities, i.e. average relative caspase activity>1, were provided when cells were exposed to 0.0015, and 0.006 mM concentrations of polyethylene glycol having a Mn of 400,000 g/mol, as indicted by the average relative caspase activity (Run 1) values.

TABLE 14

|  | POLYOX ® VSR N3000 [0.0015 mM] | POLYOX ® VSR N3000 [0.006 mM] |
|---|---|---|
| Average viability % (Run 1) | 53 | 76 |
| Standard deviation viability % (Run 1) | 15 | 15 |

The data of Table 14 illustrate that adequate viability, i.e. average viability % of 70% or greater for average viability % (Run 1) were provided after 24 hours when cells were exposed to 0.0015 and 0.006 mM concentrations of polyethylene glycol having a Mn of 400,000 g/mol.

What is claimed is:

1. A method of inducing caspase activity, the method comprising contacting a cell with a treatment compound represented by a compound of the formula:

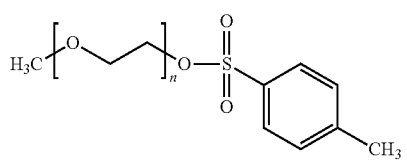

where n is from 4 to 46,000.

2. The method of claim 1, wherein the treatment compound has a number average molecular weight from 200 to 2,000,000 g/mol.

3. The method of claim 1, wherein the treatment compound has a 0.001 millimolar to 75 millimolar concentration in a treatment medium.

4. The method of claim 1, wherein the cell is a cancerous cell.

5. The method of claim 1, wherein the caspase is an effector caspase.

6. The method of claim 1, wherein the caspase is selected from caspase 3, caspase 6, caspase 7, or combinations thereof.

7. The method of claim 1, further comprising inciting apoptosis.

8. The method of claim 1, wherein the treatment compound has a number average molecular weight from 100,000 to 2,000,000 g/mol.

9. The method of claim 1, wherein the treatment compound has a 1 millimolar to 65 millimolar concentration in a treatment medium.

* * * * *